United States Patent [19]
Burakoff et al.

[11] Patent Number: 5,498,597
[45] Date of Patent: Mar. 12, 1996

[54] FKBP-13, AN FK506-BINDING IMMUNOPHILIN

[75] Inventors: Steven J. Burakoff, W. Newton; Stuart L. Schreiber, Boston; Barbara E. Bierer, Chestnut Hill, all of Mass.

[73] Assignees: Dana-Farber Cancer Institute, Inc., Boston; President and Fellows of Harvard College, Cambridge, both of Mass.

[21] Appl. No.: 822,966

[22] Filed: Jan. 17, 1992

[51] Int. Cl.$^6$ .......................... C07K 14/47; A61K 38/17
[52] U.S. Cl. .............. 514/2; 530/350; 530/324; 435/233; 435/69.1
[58] Field of Search ................... 530/324, 350; 424/94.1, 94.3; 435/69.1, 71.1; 514/12, 2

[56] References Cited

FOREIGN PATENT DOCUMENTS 0379342  1/1990  European Pat. Off. .

OTHER PUBLICATIONS

Hultsch, T., et al., (1991) Proc. Natl. Acad. Sci. USA 88:6229–33.
Dumont, F. J., et al., (1990) J. Immunol. 144:1418–24.
Schreiber, Science 251:283–287, 1991.
Harding et al., Nature 341:758–760, 1989.
Siekierka et al., Mature 341:755–757, 1989.
Michnick et al., Science 252:836–839, 1991.
Bierer et al., Eur. J. Immunol. 21:439–445, 1991.
Bierer et al., Proc. Natl. Acad. Sci. USA 87:9231–9235, 1990.
Bierer et al., Science 250:556–559, 1990.
Standaert et al., Nature 346:671–674, 1990.
Van Duyne et al., Science 252:839–842, 1991.
Wiederrecht et al., Proc. Natl. Acad. Sci. USA 88:1029–1033, 1991.
Tropschug et al., Nature 346:674–677, 1990.
Siekierka et al., J. Biological Chemistry 265:21011–21015, 1990.
Maki et al., Proc. Natl. Acad. Sci. USA 87:5443, 1990.
Lane et al., J. Protein Chemistry 10:151–159, 1991.
Palaszynski et al., Clin. Biochem. 24:63–70, 1991.
Koltin et al., Molecular and Cellular Biology 11:1718–1723. 1991.
Kay et al., Medline Immunology Today 12:137–140, 1991.
Jin et al., Proc. Natl. Acad. Sci. USA 88:6677–6681, 1991.
Liu et al., Cell 66:807–815, 1991.
Rosborough et al., Transplantation Proceedings 23:2890–2893, 1991.
Siekierka et al., Transplantation Proceedings 23:2720–2721, 1991.
Donnelly and Soldin, Transplantation Proceedings 23:2886–2889, 1991.
Brizuela et al., Mole. and Cell. Biology 11:4616–4626, 1991.
Moore et al., Nature 351:248–250 1991.

*Primary Examiner*—Garnette D. Draper
*Assistant Examiner*—David L. Fitzgerald
*Attorney, Agent, or Firm*—Fish & Richardson

[57] ABSTRACT

A purified preparation of FKBP-13, an FK506- and rapamycin-binding immunophilin; fragments and chimeras of FKBP-13 capable of binding FK506 and/or rapamycin; and DNA molecules encoding such polypeptides.

17 Claims, 3 Drawing Sheets

| | | |
|---|---|---|
| 1 | GGCCGGGGTT GACTCCGGGG GCGCGGCGAG GAGAGAC | 37 |
| 38 | ATG AGG CTG AGC TGG TTC CGG GTC CTG ACA GTA CTG TCC ATC TGC CTG AGC<br>Met Arg Leu Ser Trp Phe Arg Val Leu Thr Val Leu Ser Ile Cys Leu Ser<br>-21                                    -10 | 88 |
| 89 | GCC GTG GCC AGC ACG GGG GCC GAG GGC AAA AGG AAG CTG CAG ATC GGG GTC<br>Ala Val Ala Ser <u>Thr Gly Ala Glu Gly Lys Arg Lys Leu Gln Ile Gly Val</u><br>        -1  +1                              10 | 139 |
| 140 | AAG AAG CGG GTG GAC CAC TGT CCC ATC AAA TCG CGC AAA GGG GAT GTC CTG<br><u>Lys Lys Arg Val Asp His Cys Pro Ile Lys Ser Arg Lys Gly Asp Val Leu</u><br>                    20                          30 | 190 |
| 191 | CAC ATG CAC TAC ACG GGG AAG CTG GAA GAT GGG ACA GAG TTT GAC AGC AGC<br><u>His Met His Tyr Thr Gly Lys Leu Glu Asp</u> Gly Thr Glu Phe Asp Ser Ser<br>                            40 | 241 |
| 242 | CTG CCC CAG AAC CAG CCC TTT GTC TTC TCC CTT GGC ACA GGC CAG GTC ATC<br>Leu Pro Gln Asn Gln Pro Phe Val Phe Ser Leu Gly Thr Gly Gln Val Ile<br>            50                              60 | 292 |
| 293 | AAG GGC TGG GAC CAG GGG CTG CTG GGG ATG TGT GAG GGG GAA AAG CGC AAG<br>Lys Gly Trp Asp Gln Gly Leu Leu Gly Met Cys Glu Gly Glu Lys Arg Lys<br>                70                              80 | 343 |
| 344 | CTG GTG ATC CCA TCC GAG CTA GGG TAT GGA GAG CGG GGA GCT CCC CCA AAG<br>Leu Val Ile Pro Ser Glu Leu Gly Tyr Gly Glu Arg Gly Ala Pro Pro Lys<br>                            90 | 394 |
| 395 | ATT CCA GGC GGT GCA ACC CTG GTG TTC GAG GTG GAG CTG CTC AAA ATA GAG<br>Ile Pro Gly Gly Ala Thr Leu Val Phe Glu Val Glu Leu Leu Lys Ile Glu<br>        100                             110 | 445 |
| 446 | CGA CGA ACT GAG CTG TAACCAGACT GGGAGGGGCA GGGGAGAGGC CCCCATCAGG ACC<br>Arg Arg Thr Glu Leu<br>                120 | 503 |
| 504 | AGACTGT TCCAAAAAAA AAAAAACAAA AAACAAACAA AAAAACACTT AAAAAAAAAA AAAA | 564 |
| 565 | AAAAAA | 569 |

FIG. 1

| | | |
|---|---|---|
| FKBP-13 | MRLSWFRVLTVLSICLSAVASTGAEGKRKL | 9 |
| FKBP-12 | MG | 2 |
| FKBP-13 | QIGVKKRVDHCPIKSRKGDVLHMHYTGKLE | 39 |
| FKBP-12 | VQVETISPGDGRTFPKRGQTCVVHYTGMLE | 32 |
| FKBP-13 | DGTEFDSSLPQNQPFVFSLGTGNVIKGWDN | 69 |
| FKBP-12 | DGKKFDSSRDRNKPFKFMLGKQEVIRGWEE | 62 |
| FKBP-13 | GLLGMCEGEKRKLVIPSELGYGERGAPPKI | 99 |
| FKBP-12 | GVAQMSVGQRAKLTISPDYAYGATGHPGII | 92 |
| FKBP-13 | PGGATLVFEVELLKIERRTEL | 120 |
| FKBP-12 | PPHATLVFDVELLKLE | 108 |

FKBP-13, AN FK506-BINDING IMMUNOPHILIN

This invention was made in the course of work supported by National Institutes of Health Grants PO1 CA39542 and GM38627; the U.S. Government therefore has certain rights in the invention.

BACKGROUND OF THE INVENTION

The field of the invention is immunophilins.

FK506, rapamycin, and cyclosporine A (CsA) are immunosuppressive agents recently shown to inhibit signal transduction pathways following binding to cytoplasmic receptors termed immunophilins (Schreiber, Science 251:283–287, 1991). When complexed with an immunophilin, each of FK506 and CsA apparently interferes with cytoplasmic signaling pathways leading to transcription in the T cell (Dumont et al., J. Immunol 144:251–258, 1990; Bierer et al., Proc. Natl. Acad. Sci. U.S.A. 87:9231–9235, 1991). In contrast, rapamycin bound to an immunophilin inhibits a lymphokine-dependent signaling pathway in the T cell that, if not so inhibited, leads to proliferation of the cell.

The predominant FK506- and rapamycin-binding immunophilin in human T cells is the 12 kDa cytosolic receptor variously termed "FKBP" or "HCB" (and hereinafter referred to as FKBP-12) (Harding et al., Nature 341:758–760, 1989; Siekierka et al., Nature 341:755–757, 1989; European patent application publication number 0379342: each of which publications is herein incorporated by reference). Each of the latter two references sets forth the nucleotide sequence of the cDNA encoding FKBP-12, as well as the deduced amino acid sequence. Although FKBP-12 catalyzes the interconversion of cis and trans rotamers of peptidyl-prolyl amide bonds of peptides, and binding to FK506 or rapamycin inhibits this activity of FKBP-12, inhibition of this rotamase activity was shown to be insufficient for mediating the actions of FK506 and rapamycin in T cells (Bierer et al., Proc. Natl. Acad. Sci. U.S.A. 87:9231–9235, 1990; Bierer et al., Science 226:556–559, 1990). Recent studies show that the same is true of the rotamase activity of human cyclophilin (Sigal et al., J. Exp. Med. 173:619–628, 1991), which is the predominant CsA-binding protein in human T cells (Handschumacher et al., Science 226:544–546, 1984).

Van Duyne et al. (Science 252:836, 1991) have published an x-ray crystallographic study of FKBP-12 complexed with FK506. The following passages and the enclosed FIGS. 7, 8A and 8B are taken from pages 840–841 of this article (citations inserted):

> The protein component . . . is a five-stranded antiparallel β sheet wrapping with a right-handed twist around a short α helix. The five-stranded antiparallel β-sheet framework includes residues 2 to 8, 21 to 30, 35 to 38 with 46 to 49, 71 to 76, and 97 to 106 (Surface areas and secondary structure were calculated with the program DSSPNOV (Kabecha and Sander, Biopolymers 22:2577, 1983) with topology +3, +1, −3, +1 (Richardson, Nature 268:495, 1977). The α helix is formed by residues 57 to 63. Thus, the fold of the protein is identical to that independently seen in the solution structure of uncomplexed FKBP (Michnick et al., Science 252:836, 1991).
>
> FK506 binds in a shallow cavity between the α helix and the β sheet, with roughly 430 Å$^2$ (50%) of the ligand surface being buried at the protein-ligand interface and the remainder, encompassing the region around the allyl and the cyclohexyl groups, being exposed to solvent. Loops composed of residues 39 to 46, 50 to 56, and 82 to 95 flank the binding pocket, which is lined with conserved, aromatic residues. The side chains of Tyr$^{26}$, Phe$^{46}$, Phe$^{99}$, and Val$^{55}$-Ile$^{56}$ make up the sides of the pocket, while the indole of Trp$^{59}$, in the α helix, is at the end of the pocket and serves as platform for the pipecolinyl ring, the most deeply buried part of FK506 . . . Both the location and the orientation of the pipecolinyl ring are consistent with NOEs observed between FK506 and Trp$^{59}$, Phe$^{46}$, and Tyr$^{26}$ (Wandless et al., J. Am. Chem. Soc. 113:2339, 1991). As might be expected, there are no water molecules in the hydrophobic binding pocket.
>
> There are five hydrogen bonds between FKBP and FK506: Ile$^{56}$-NH to C-1 lactone carbonyl, Glu$^{54}$-CO to C-24 hydroxyl, Gln$^{53}$-CO to C-24 hydroxyl (through a water molecule), Asp$^{37}$-CO$_2^-$ to C-10 hemiketal hydroxyl, and Tyr$^{82}$-OH to C-8 amide oxygen. The first three, involving residues near the NH$_2$-terminus of the helix, form an array reminiscent of the antiparallel sheet interactions in many peptide-protein (especially protease) complexes, suggesting that the region of FK506 spanning C-24 to C-1 through the lactone linkage may mimic a dipeptide. As has been noted (Albers et al., J. Org. Chem. 55:4984, 1990), the adjacent pyranose-pipecolinyl region also resembles a dipeptide, and thus FK506 may prove to be an illustrative example of extended peptidomimicry. The fifth hydrogen bond, involving the C-8 amide, is the most conspicuous because it is nearly orthogonal to the carbonyl plane and thus may be relevant to the mechanism of rotamase activity.
>
> Protein-protein hydrogen bonds help maintain the organization of the binding pocket, particularly in restraining the flexible loops, which assume well-defined conformations in the complex. For instance, Asp$^{37}$-CO$_2^-$ forms hydrogen bonds not only with the C-10 hemiketal hydroxyl of FK506, but also with the Arg$^{42}$ and Tyr$^{26}$ side chains (Horovitz et al., J. Mol. Biol. 216:1031, 1990). Two well-ordered water molecules bridge the loop from Tyr$^{82}$ to Ala$^{95}$ by mediating hydrogen bonds from Tyr$^{82}$-NH to Ala$^{95}$-CO and from Gly$^{83}$-CO to Pro$^{92}$-CO. Three residues within this loop, Tyr$^{82}$, His$^{87}$, and Ile$^{91}$, contact FK506, with the side chains of the latter two forming a surface complementary to the pyranose methyl group region. The observed loop geometry thus plays a major role in ligand binding, but it also forces Ala$^{81}$ to adopt unfavorable φ, Ψ values of −141° and −120° respectively.

A number of cyclophilins associated with subcellular organelles have been reported. These include the cyclophilin-like protein encoded by the gene nina A of *Drosophila melanogaster* (Shieh et al., Nature 338:67–70, 1989; Schreuwly et al., Proc. Natl. Acad. Sci. U.S.A. 86:5390–5394, 1989). The Nina A gene product has an N-terminal signal sequence and a C-terminal hydrophobic domain that may serve as a membrane anchor. Mutations in this gene result in photoreceptor cell dysfunction that may be due to improper trafficking of rhodopsin molecules. A yeast cyclophilin with a signal sequence has also been described (Koser et al., Nucleic Acids Res. 18:1643, 1990), and recently a human cyclophilin with a signal sequence and with sequence similarity to this yeast cyclophilin has been cloned (Price et al., Proc. Natl. Acad. Sci. U.S.A. 88:1903–1907, 1991).

FKBP-12 is the protein responsible for mediating the potent anti-proliferative actions of rapamycin in yeast. Deletion of the FKBP-12 gene in *Saccharomyces cerevisiae* results in rapamycin-resistant strains of yeast; rapamycin sensitivity is returned following transfection of either yeast or human FKBP-12 into the rapamycin-resistant mutant cells (Koltin et al., Mol. Cell. Biol. 11:1718–1723, 1991). Similar findings can be inferred from the studies of cyclophilin in two lower eukaryotes (Tropschug et al., Nature 342:953–955, 1989).

SUMMARY OF THE INVENTION

Applicants have determined that a second FK506-and rapamycin-binding protein, distinct from FKBP-12, is present in mammalian cells; this protein has been termed FKBP-13. A cDNA encoding human FKBP-13 (SEQ ID NO: 1) has been cloned, sequenced and expressed; in addition, FKBP-13 from calf thymus has been purified and partially sequenced (SEQ ID NO: 4). It is expected that all mammalian species, and probably most or all eukaryotic species, contain an FKBP-13, herein defined as a naturally-occurring protein which (1) binds FK506, and (2) has at least 80% sequence identity with (i.e., contains amino acids that match up with at least 80% of the amino acids of) human FKBP-13. A preparation of FKBP-13 (preferably free of other proteins of eukaryotic origin) may be produced by isolation of FKBP-13 from a natural source (e.g., eukaryotic cells such as mammalian T cells) or by synthetic means, but preferably is obtained by recombinant means: by expression of a cloned cDNA or genomic DNA encoding FKBP-13. The latter method would include the steps of provided a cell (or an essentially homogeneous population of cells, i.e. a population which is a clone of cells derived from a single cell) which contains an isolated DNA having a nucleotide sequence encoding FKBP-13 (e.g., with essentially the amino acid sequence given in FIG. 1, SEQ ID NO:1); growing that cell or cells in a medium to form a population of cells which express the isolated DNA (i.e., which transcribe the isolated DNA into mRNA, and then translate the mRNA into protein); and purifying FKBP-13 from the population of cells, or from the medium bathing the cells (e.g., by means of a rapamycin affinity column as described below). The invention includes a substantially purified preparation of an FKBP-13, which means a preparation less than 1% of which is protein other than FKBP-13. This FKBP-13 is preferably of molecular weight less than 16 kDa and more preferably between 10 and 15 kDa. The amino acid sequence of the portion of this FKBP-13 corresponding to amino acids 33 through 115 of human FKBP-13 is preferably at least 90% identical to this portion of human FKBP-13, and more preferably at least 95% identical. By "isolated DNA having a nucleotide sequence encoding FKBP-13" is meant a segment of DNA encoding FKBP-13, but which is free of the genes that, in the naturally-occurring genome of the organism from which the segment is derived, flank the gene encoding FKBP-13); the nucleotide sequence encoding FKBP-13 may be any sequence which encodes a protein within the definition of FKBP-13, but is preferably one which encodes the human form of FKBP-13, and more preferably is one which contains essentially the nucleotide sequence given in FIG. 1 (SEQ ID NO:1).

The ability of FKBP-13 to bind rapamycin and FK506 can be exploited in a drug screening program designed to identify new immunosuppressant drugs. Such a screening program would include the steps of identifying a candidate compound (whether naturally-occurring or synthetic) suspected of having immunosuppressant activity; contacting that compound with a screening reagent (such as a solid matrix material) that includes FKBP-13, or a rapamycin- or FK506-binding fragment thereof; and determining (for example, by competition with labelled rapamycin, FK506, or antibody specific for an epitope within the FK506-binding region of FKBP-13) whether the candidate compound binds to the screening reagent, such binding being an indicator of the potential immunosuppressant activity of the candidate compound. This, of course, would be just one preliminary step in identifying new immunosuppressant drugs, but it would be a simple, quick and inexpensive means of screening large numbers of possible candidates in order to identify a few for further study.

FKBP-13 (or a rapamycin- or FK506-binding fragment thereof) in combination with an immunosuppressant drug which binds to it (such as rapamycin or FK506) also may have therapeutic applications. Because it is thought that drugs of the class of rapamycin and FK506 require FKBP-13 in order to exert an effect on T-cells, it is proposed that FKBP-13 bound to such a drug (presumably at a ratio of 1:1 drug to FKBP-13) and dissolved or suspended in a suitable pharmaceutically-acceptable carrier would be useful for the treatment of such indications as autoimmune diseases (e.g., rheumatoid arthritis and type I diabetes), organ transplant rejection, and graft vs. host disease. The combination of the two molecules may have a more potent antiproliferative effect on target cells than does the drug alone, for FKBP-13 is normally present in relatively low levels in cells and may thus be a limiting factor in drug-induced immunosuppression. In addition, the combination of FKBP-13 bound to an immunosuppressant drug can be used to investigate the nature of the cellular constituent to which the duo binds in vivo in order to effect immunosuppression, (e.g., by fixing FKBP-13, or a hybrid molecule including at least the FK506-binding portion of FKBP-13, to a matrix material, binding rapamycin or FK506 to the FKBP-13, and then testing various biological samples to find any components of such samples that bind to the FKBP-13/drug complex. Such components can then be tested to see whether they also bind to FKBP-13 without the drug). These assays would lead to further information about the mechanism of immune reaction and possible means to control it. The invention thus includes a method in which FKBP-13 bound to rapamycin, FK506, or another FKBP-13-binding immunosuppressant drug to form a first complex, and is contacted with a mammalian cellular constituent (e.g., a protein which has been dissolved in a solution, or which is integrated into a membrane or in an intact cell) which binds to the first complex to form a second complex.

Alternatively, FKBP-13 may have therapeutic or diagnostic applications even without the addition of an immunosuppressive drug to which the protein binds.

The cloning of a cDNA encoding FKBP-13 permits routine, genetically engineered manipulations of the amino acid sequence, including deletions, substitutions, and additions at defined sites. By engineering deletions of particular regions of the DNA in accordance with the guidance provided herein, DNA encoding various fragments of FKBP-13, including fragments which can bind rapamycin and/or FK506, would result; expression of these DNAs would produce fragments of FKBP-13 capable of binding rapamycin, FK506, and other immunosuppressant drugs, which fragments could replace intact FKBP-13 in the methods and compositions outlined above. Such fragments would, because of their smaller size, be easier to introduce into a cell than would be intact FKBP-13. Alternatively, FKBP-13 or a fragment thereof could be packed into liposomes, using standard techniques, in order to get the polypeptide through the cell membrane. The liposomes could be targeted into specific cells, such as T-cells, by attaching to the surface of the liposomes a monoclonal antibody that is specific for a cell-surface receptor, such as the so-called T-cell receptor, which is modulated upon binding by its antibody. Methods for accomplishing this are well known to those of ordinary skill in the art of liposome technology.

Other features and advantages of the invention will be apparent from the following detailed description, and from the claims.

DETAILED DESCRIPTION

The drawings are first described.

Drawings FIG. 1 (SEQ ID NO: 1) is a representation of the nucleotide sequence and corresponding predicted encoded amino acid sequence of a cDNA encoding FKBP-13. Arrow denotes the signal peptide cleavage site; the N-terminal sequence obtained from bovine thymus FKBP-13 by protein microsequencing is underlined; a possible polyadenylation signal (ACAAA) is shown in bold face (nucleotides 537–541); and the italicized amino acids represent the putative ER retention sequence.

FIG. 2 is a northern blot analysis of FKBP-13 mRNA. The total RNA and poly (A)$^+$ RNA from human Jurkat T cells and human JY B cells were electrophoresed on a 1.6% agarose gel, blotted to a nitrocellulose membrane, and hybridized with the FKBP-13 cDNA probe. The FKBP-13 mRNA is indicated by an arrow. Lane 1, total Jurkat T cell RNA; lane 2, poly (A)$^+$ Jurkat T cell RNA; lane 3, total JY B cell RNA; lane 4, poly (A)$^+$ JY B cell RNA.

FIG. 3 is an SDS-PAGE analysis of the products of in vitro translation of FKBP-13 cDNA (SEQ ID NO: 1) (lanes 1 and 2), and the subcellular localization of FKBP-13 (lanes 3–7). FKBP-13 cDNA (SEQ. ID NO: 1) was transcribed by T7 RNA polymerase in vitro. Synthetic RNA was translated using reticulocyte lysate in the absence (lane 1) or presence (lane 2) of canine pancreatic microsomal membranes. Samples were analyzed by reducing SDS/14% PAGE and autoradiographed. Subcellular localization of FKBP-13 (Lanes 3–7): [$^{35}$S]methionine-labeled human Jurkat T cells were fractionated by centrifugation; FKBP-13 and FKBP-12 were extracted by an FK506 affinity matrix, eluted by an FK506 solution, and analyzed by reducing SDS/14% PAGE. The gel was dried and autoradiographed. Lane 3, whole cell lysate; lane 4, cytosolic fraction; lane 5, crude nuclei; lane 6, heavy membrane; lane 7, light membrane. Bands corresponding to FKBP-13 and FKBP-12 are indicated by arrows. The protein molecular weight markers (Bio-Rad) are lysozyme (14.4 kDa), soybean trypsin inhibitor (21.5 kDa), carbonic anhydrase (31.0 kDa), ovalbumin (42.7 kDa), bovine serum albumin (66.1 kDa), phosphorylase B (97.4 kDa).

FIG. 4 is an SDS-PAGE analysis of FKBP-13 in Jurkat T cell culture medium. [$^{35}$S]methionine-labeled human Jurkat T cells were incubated in 5 ml RPMI 1640 medium (5% FCS) for 2 hours (lane 1) and 5 hours (lane 2). The supernatant and the pelleted, fragmented cells were extracted with the rapamycin affinity matrix; the bound protein was directly analyzed by reducing SDS/14% PAGE. Lane 3, whole cell lysate; lane 4, cytosolic fraction; lane 5, crude nuclei; lane 6, heavy membrane; lane 7, light membrane. The protein molecular weight markers and labels for FKBP-12 and FKBP-13 are the same as described above.

FIG. 5 is a representation of the molecular structure of human FKBP-12 (alpha-carbon only), used as a model of the structure of FKBP-13. Gly-12 and Ser-67 of FKBP-12, which align with Cys-20 and Cys-75 of FKBP-13, respectively, have been modified to incorporate the thiomethyl side chain of a cysteine residue with the natural stereochemistry. It is seen that the thiol groups (dark circles) are within disulfide bonding distance. The putative ER-retention sequence is anticipated to project away from the edge of the 5-stranded beta-sheet (from the C-terminus of FKBP-12) to be available for interactions with the receptor for the ER-retention signal peptide.

FIG. 7 is a stereo view of the FKBP-12/FK506 complex, showing a Cα tracing for the protein with bound FK506 and aromatic side chains of the binding pocket (as published in Van Duyne et al., Science 252:839, 840, 1991).

FIG. 8A is a stereo view of the binding region of FKBP-12 complexed with FK506, showing FK506 and selected residues of the hydrophobic binding pocket.

FIG. 8B is a stereo view of a selected region of electron density in the binding pocket showing the pipecolinyl ring, the C-8 amide and C-9 keto carbonyls, and the three aromatic residues that make up the C-9 carbonyl binding pocket.

EXPERIMENTAL

Figure 2:
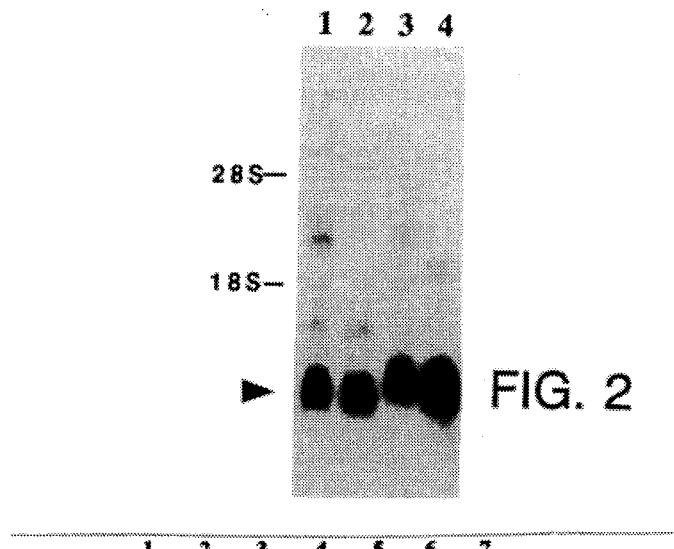

Determination of the N-terminal sequence of FKBP-13.

Homogenized calf thymus (Arlene & Sons, Hopkinton, Mass.) extract (200 ml) was passed through —0.1 ml of a rapamycin affinity matrix, and the matrix was washed as previously described (Fretz et al., J. Am. Chem. Soc. 113:1409–1411, 1991; herein incorporated by reference). The matrix was then incubated with 250 μl of a methanolic solution of FK506 (10 mg/ml) at 4° C. The eluate was electrophoresed on a 12% polyacrylamide gel. The proteins were electroblotted onto a PVDF membrane (Millipore, Milford, Mass.) (Fretz et al., 1991), and the $M_r$~15,000 band was visualized by Coomassie blue staining, excised, and subjected to Edman degradation microsequencing (Matsudaira, J. Biol. Chem. 262:10035–10038, 1987) .

PCR cloning of a fragment of the FKBP-13 cDNA.

Based on the 40-amino acid N-terminal sequence of FKBP-13, two PCR primers were synthesized:
5'-GA(A/G)GG(T/G)AA(A/G)    (C/A)G(G/A/T/C)AA(A/G)C(C/T)-3' (SEQ ID NO: 2), and
5'    -CC(G/A/T/C)GT(A/G)TA(A/G)TGCAT(A/G)TG-3' (SEQ ID NO: 3).
Using these two primers and cDNA prepared from 100 ng of human Jurkat T cell total RNA (see below), a 90 bp fragment was amplified, subcloned into plasmid Bluescript (Stratagene, La Jolla, Calif.) by blunt end ligation, and sequenced (Sequenase System, U.S. Biochemical, Cleveland, Ohio).

Cloning and sequencing of the full-length cDNA encoding FKBP-13.

A human colon carcinoma (λgt11) cDNA library was screened for FKBP-13 cDNA using the 90 bp fragment described above. Filters were hybridized at 42° C. in 50% (V/V) formamide/5× SSC/5× Denhardt's/50 mM sodium phosphate (pH 6.5)/0.1% SDS, and washed at 24° C. in 2× SSC/0.1% SDS for 30 minutes and at 65° C. in 1× SSC/0.1%

SDS for 1 hr. From a total of 2×10⁵ phage plaques, three positive clones were obtained. The 0.6 kb EcoR1 insert was subcloned into plasmid Bluescript, and double strand sequencing was performed. The University of Wisconsin GCG programs (Devereux et al., Nucl. Acids Res. 12:387–395, 1984) were used to search for homologous sequences and align the sequences of FKBP-12 and FKBP-13.

Northern Blot Analysis.

Total RNA was prepared from Jurkat T cells and JY B cells by the guanidinium method (Sambrook et al., Molecular Cloning: A Laboratory Manual, Cold Spring Harbor Laboratory, Cold Spring Harbor, N.Y., 1989). Poly A RNA was enriched by oligo dT cellulose chromatography. RNA was electrophoresed on a 1.6% formaldehyde gel, transferred to nitrocellulose, and hybridized with random-primed FKBP-13 cDNA (SEQ ID NO: 1) (Sambrook et al., 1989) in 50% formamide, 5× SSC, 5× Denhardt's solution, 50 mg/ml salmon sperm DNA, 50 mM $K_3PO_4$ (pH 7.4) at 42° C. for 16–20 hours. The low-stringency wash conditions were 2× SSC, 0.1% SDS for 15–30 minutes at room temperature, followed by 0.5× SSC, 0.1% SDS for 15–30 minutes at room temperature. The high-stringency wash was followed by 0.1× SSC, 0.1% SDS at 50° C. for 60 minutes.

Functional determination of the gene product from FKBP-13 cDNA.

FKBP-13 RNA was prepared from BamH1 linearized FKBP-13 cDNA (SEQ ID NO: 1) using T7 RNA polymerase (Stratagene) in the presence of G(5')ppp(5')G. RNA was translated in vitro using the rabbit reticulocyte lysate system in the presence of [$^{35}$S]methionine, and repeated in the presence of canine pancreatic microsomal membranes (Promega, Madison, Wis.). These products were electrophoresed on a 14% SDS polyacrylamide gel. The products of both reactions were incubated with 20 µl of rapamycin affinity matrix overnight at 4° C. After washing the matrix, the bound proteins were eluted using a methanolic solution of rapamycin (10 mg/ml) at 4° C. for 2 hours (Fretz et al., 1991). The supernatants were electrophoresed on polyacrylamide gels; the gels were dried at 80° C. for 1 hr and autoradiographed at −70° C. on Kodak XAR-film.

Assay for FKBP-13 secretion.

Jurkat T cells (2.5×10⁶) were labeled with 5 mCi [$^{35}$S] methionine for 2 hours in methionine-free medium (New England Nuclear, Boston, Mass.), washed, and cultured in 5 ml RPMI 1640 (M.A. Bioproducts, Walkersville, Md.) with 5% FCS for either 2 or 5 hours. The cell lysate and culture medium were separately incubated with the rapamycin affinity matrix as described above. These samples were analyzed by SDS/PAGE and autoradiography as described above.

Subcellular fractionation of Jurkat T cells.

Jurkat T cells (2×10⁸) were labeled in vivo with [$^{35}$S] methionine as described above. After washing, the cells were incubated in 2 ml hypotonic buffer (42 mM KCl, 10 mM HEPES (pH 7.4), 5 mM $MgCl_2$) for 15 minutes at 4° C. The cells were passed through a 30 gauge needle five times. The extract was centrifuged at 200× g for 10 minutes at 4° C. to pellet the nuclei. The supernatant was centrifuged at 10,000× g for 10 minutes to collect the heavy membrane fraction, and at 150,000× g for 90 minutes to collect the light membrane fraction; the remaining supernatant was collected as the cytoplasmic fraction. The unfractionated cells, nuclei, heavy and light membrane fractions were lysed for 30 minutes at 4° C. in 1 ml lysis buffer (1% NP40, 10 mM Tris (pH 7.4), 0.15 M NaCl, 1 mM EDTA, 5 nM 2-mercaptoethanol, 1% BSA, 2 mM PMSF, and 50 mM NaF). Cellular debris was removed by centrifugation at 16,000× g for 15 min at 4° C. These fractions were analyzed with a rapamycin affinity matrix as described above.

RESULTS

Isolation of the human FKBP-13 cDNA.

Using a rapamycin affinity matrix, a protein ($M_r$~15,000 on a 12% polyacrylamide gel) was isolated from bovine thymus tissue extracts (Fretz et al., 1991), and the N-terminal sequence TGTEGKRKLQIGVKKRVDHCPIKSRKGD-VLHMHYTGKLED (SEQ ID NO: 4) was determined. Based on this 40-amino acid N-terminal sequence, two degenerate oligonucleotide primers were synthesized for subsequent PCR reactions. A 90 bp PCR fragment was generated, subcloned, sequenced, and used to screen a human λgt11 cDNA library from a human colon carcinoma cell line. From each of three positive clones, the same 0.6 kb insert was isolated. This insert was subcloned into plasmid Bluescript and sequenced (FIG. 1; SEQ ID NO: 1). The 570 bp sequence of this cDNA contains an open reading frame of 423 nucleotides, which begins at a translation initiation ATG codon and ends at a TAA termination codon. The open reading frame is flanked by 37 nucleotides of 5' untranslated sequence and 110 nucleotides of 3' untranslated sequence. The poly A tail begins at nucleotide 551. The N-terminal 40 amino acids (SEQ ID NO: 4) of the protein from bovine thymus precisely match the predicted amino acid sequence from nucleotide 101, which is 60 nucleotides downstream from the translation initiation codon, to nucleotide 221. The first 21 amino acids encoded by the open reading frame, which contains 13 hydrophobic residues, may constitute a signal peptide. The carboxy terminal 4 amino acids, (amino acids 117–120 of SEQ. ID NO: 1) may encode an endoplasmic reticulum retention sequence (Pelham, TIBS, 15:483–486, 1990). No internal hydrophobic region that could serve as a transmembrane segment is present. The mature protein of 120 amino acids has a predicted MW of 13.2 kDa.

Homology between FKBP-13 and FKBP-12. A computer search of both protein and cDNA databases revealed that this 13 kDa protein sequence (SEQ ID NO: 1) is highly homologous only with FKBP-12 (SEQ ID NO: 5), differing substantially from any other proteins or protein segments. Although the N-terminal portions of FKBP-12 and FKBP-13 show little homology (see FIG. 6), overall FKBP-13 has 51% nucleotide sequence identity and 43% amino acid sequence identity with FKBP-12. The region of highest homology begins with Ser-25 of FKBP-13 and with Pro-17 of FKBP-12, and ends at the C-terminus of FKBP-12, leaving the last five amino acids of FKBP-13 unmatched. Of the 92 C-terminal amino acids of FKBP-13, 46 are identical to, and 20 are conservative replacements of, their counterparts in FKBP-12. All residues conserved in all known sequences of FKBP-12 are conserved in FKBP-13. Structural studies of free FKBP-12 and of FKBP-12 bound to FK506 have implicated roles for these conserved residues in drug binding and/or rotamase catalysis, suggesting that FKBP-13 also has rotamase activity.

Neither human FKBP-12 nor human FKBP-13 has sequence similarity with any cyclophilin. Allowing for a single deletion at position 338 in a cryptic sequence from *N. meningitidis*, each of FKBP-13 and FKBP-12 shares 49% sequence identity with an open reading frame from *N. meningitidis* in their C-terminal regions (data not shown).

FKBP-13 is transcribed at approximately equal levels in T cells and B cells. To investigate the expression of the gene encoding FKBP-13 in lymphocytes, northern blot analyses were performed using the FKBP-13 cDNA (SEQ ID NO: 1) as a probe (FIG. 2). Under high-stringency wash conditions, the predominant band which hybridized to the probe appeared at 0.6 kb. The 0.6 kb band was almost equally abundant in RNA preparations from T and B lymphocytes. The intensity of the ethidium bromide-stained rRNA was similar in the two non-poly A-selected preparations, indicating that similar amounts of total RNA were loaded onto the gel. When northern blotting was performed using low-stringency wash conditions (data not shown), several weak bands were detected in both the total and poly A RNA preparations, including a 1.6 kb band that may be the FKBP-12 mRNA cross-hybridized to the FKBP-13 cDNA probe.

In vitro transcription and translation of FKBP-13 cDNA.

Figure 3:
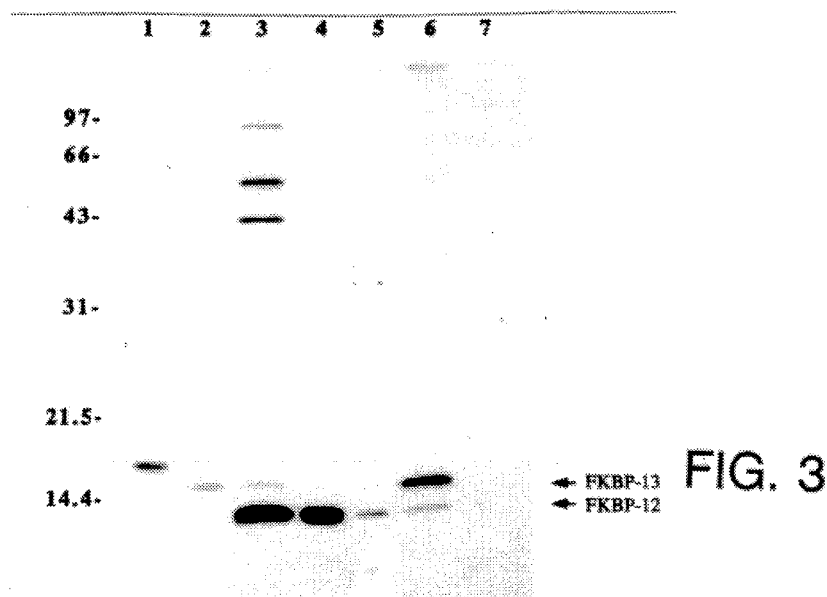

To demonstrate that the first 21 amino acids encoded by the open reading frame of the FKBP-13 cDNA is a signal peptide that can be cleaved by a signal peptidase, the mRNA of FKBP-13 was synthesized in vitro by T7 RNA polymerase and then expressed in an in vitro reticulocyte translation system (Stratagene, LaJolla, Calif.). In the presence of canine pancreatic microsomal membranes, which contain signal peptidase activity, a mature protein was synthesized and migrated as a $M_r \sim 15{,}000$ band on a 14% SDS polyacrylamide gel (FIG. 3, lane 2); while in the absence of the microsomal membranes, a precursor protein was detected as an $M_r \sim 17{,}000$ band (lane 1). The cleavage was almost complete within a 1 hour incubation. Both precursor and mature forms of FKBP-13 bind to FK506 and rapamycin affinity matrices, and can be eluted with the respective drug (data not shown).

Subcellular localization of FKBP-13.

Figure 4:
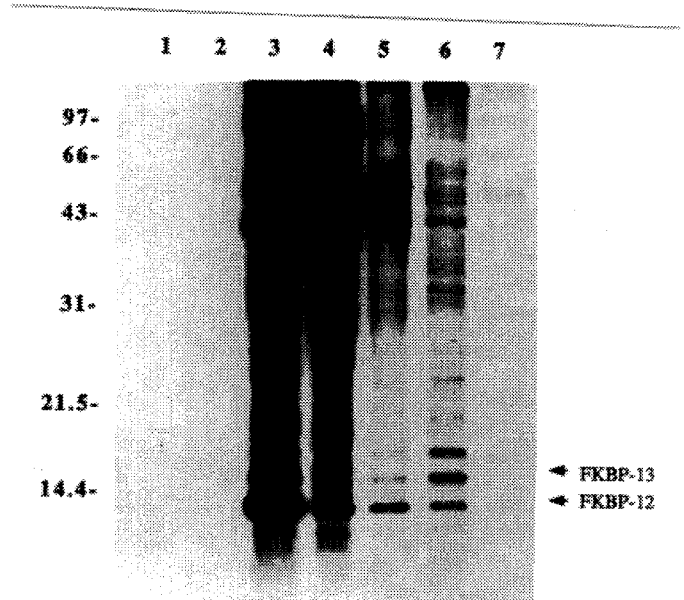

To determine if FKBP-13 is a secreted protein, [$^{35}$S] methionine-labeled Jurkat T cells were incubated for 2 hours (lane 1) and 5 hours (lane 2) in non-radioactive medium (FIG. 4). The cells were pelleted, and the culture supernatant was incubated with rapamycin affinity matrix. Proteins were eluted with rapamycin at 1 mg/ml. No radioactive protein bands were detected by autoradiography from the affinity matrix eluates (lanes 1 and 2). Neither FKBP-13 nor FKBP-12 was secreted into the culture medium, even after 5 hours of incubation. The cell pellet contained both FKBP-12 and FKBP-13 (lane 3). In these experiments, because the matrix was not eluted by drug, more protein bands were observed with SDS-PAGE compared with FIG. 3. Several other protein bands seen in these gels might be additional FKBP family members.

To determine the intracellular location of FKBP-13, Jurkat T cells were [$^{35}$S]methionine-labeled, lysed in hypotonic solution, and fractionated by centrifugation into cytosolic, crude nuclear, heavy membrane and light membrane fractions. The FK506-binding proteins were extracted from these fractions and from the whole cell lysate by FK506 affinity matrix, and then run on SDS-PAGE. FKBP-13 extracted from the whole cell lysate appeared as an $M_r \sim 15{,}000$ band on SDS polyacrylamide gel (FIG. 3, lane 3), comigrating with in vitro-synthesized mature FKBP-13 (lane 2). FKBP-13 was enriched in the heavy membrane fraction (lane 6), which includes most of the mitochondrial and lysosomal membranes and some microsomal membranes. FKBP-12 is predominantly a cytoplasmic protein (lane 4). The small amount of FKBP-13 in the cytosolic (lane 4) and nuclear fractions (lane 5), and also the small amount of FKBP-12 in nuclear and heavy membrane fractions, most likely resulted from cross-contamination. Thus, we conclude that FKBP-12 is the major cytoplasmic FKBP in T cells, while FKBP-13 is an intracellular membrane-associated FKBP.

The presence of a signal sequence for FKBP-13 indicates that it may be localized to a compartment with an oxidizing environment, which promotes the formation of disulfide bonds. FKBP-13 has two cysteine residues, Cys-20 and Cys-75, that are not conserved in FKBP-12; they correspond to Gly-12 and Ser-67 in FKBP-12. However, if two cysteine side chains are added onto the X-ray structure of FKBP-12 in place of the side chains of Gly-12 and Ser-67 (FIG. 5), they are found to be within disulfide bond-forming distance. Thus, we postulate that there is a disulfide linkage involving Cys-20 and Cys-75 in the structure of FKBP-13. In fact, this putative disulfide is located at an unusual topological feature of the structure of FKBP-12: a crossing of two loops that connect four strands of a five-stranded antiparallel beta sheet. FKBP-2 has a number of backbone-backbone and backbone-side chain hydrogen bonds and van der Waals contacts that stabilize this topology. The sequences of FKBPs are not highly conserved around Cys-20, which is part of the divergent N-terminal region, or around Cys-75. Thus, the putative disulfide bond may be critical for stabilizing this unusual topological feature in FKBP-13.

IgE receptor-mediated exocytosis in mast cells is inhibitable by FK506 (data not shown). Affinity chromatography of lysates from RBL cells (a rat mast cell line) indicates that FKBP-13 is the predominant FK506- and rapamycin-binding protein in this cell type. Therefore, FKBP-13 is a likely candidate to be a mediator of the actions of FK506 in mast cells.

Other Embodiments

Assay for cis-trans isomerase activity

The presumed cis-trans isomerase activity of FKBP-13, or of any stable fragment of FKBP-13, can be tested by the procedure of Fischer et al., Nature 337:476–478, 1989, or of European Patent Application No. 0,379,342, each of which is incorporated by reference herein.

Preparation and testing of FKBP-13 fragments capable of binding FK506 or rapamycin Fragments of any FKBP-13 isoform can be prepared by routine methods, including proteolytic cleavage of the protein, de novo synthesis of the fragment, or genetic engineering. The latter method would involve, for example, preparation of a DNA encoding the desired fragment (e.g., by appropriate restriction digestion of the FKBP-13 DNA disclosed herein, or by de novo synthesis of the DNA encoding the fragment), inserting the DNA into an expression vector, and expressing the DNA in an appropriate expression system. The fragments can be conveniently purified by use of a rapamycin or FK506 affinity column, as described above. These manipulations are well within the abilities of one of ordinary skill in the art of genetic engineering.

Figures 5, 6:
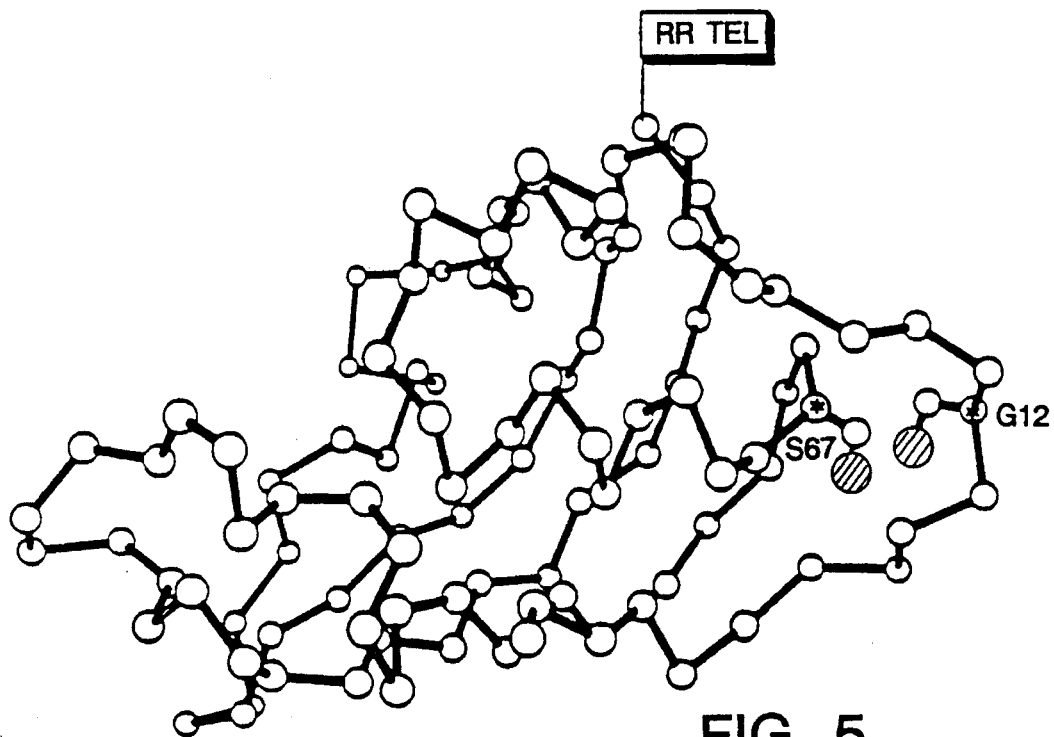
FIG. 6 is a protein sequence alignment of precursor human FKBP-13 (i.e., human FKBP-13 including its leader peptide) and FKBP-12, wherein vertical bars denote amino acid identity and the arrow denotes the signal peptide cleavage site of FKBP-13.

The disclosures set forth herein, combined with published information about the active site of the related protein, human FKBP-12 (e.g., Michnick et al., Science 252:836, 1991, herein incorporated by reference; and the information taken from Van Duyne et al., Science 252:836, 1991, which is set forth herein), provides ample guidance for one of ordinary skill to design fragments of FKBP-13 that are capable of binding rapamycin and/or FK506 under conditions permitting binding of such drug(s) to FKBP-13. A comparison of the amino acid sequences of FKBP-13 and FKBP-12, as shown in FIG. 6, indicates that there is a high degree of homology in the region corresponding to amino acids 33–115 of FKBP-13, with only one matched site outside of this region. The region of high homology contains the active site of each of FKBP-12 and -13, and presumably of any rapamycin- or FK506-binding FKBP-13 homolog. Therefore, this region will be retained in relatively intact form in any FKBP-13 fragment which has biological activity, with no more than three additional amino acids deleted from either end of this core region. The resulting fragments that retain the ability to bind rapamycin and/or FK506 will thus contain, at a minimum, a portion of an FKBP-13 homolog corresponding to amino acids 36–112 of human FKBP-13, and may contain up to all but one of the rest of the amino acid residues of the intact protein. Examples of such fragments include but are not limited to polypeptides having amino acids 2–120, 3–120, 4–120, 18–120, 27–120, 33–120, 36–120, 1–119, 1–118, 1–115, 1–112, 2–119, 10–115, 20–115, 30–115, 33–115, and 36–112. In addition, fragments within the invention could have interior deletions of one or more amino acids from outside the core region: e.g., polypeptides having a deletion of those amino acids corresponding to residues 2–20, 10–32, 112–119, or perhaps only residue 16. These are given merely as illustrative examples of fragments expected to retain the ability of FKBP-13 to bind immunosuppressive drugs, and are in no way intended to limit the invention. Preferably, such fragments will retain at least 50% of the intact protein's affinity for rapamycin and/or FK506, as measured by $K_D$, and more preferably, such fragments will retain at least 90% of such affinity. A fragment such as a polypeptide containing amino acids 36 to 112 of human FKBP-13 could be engineered to include an additional sequence of at least ten amino acids not corresponding to any portion of human FKBP-13.

Also within the invention are chimeras of human FKBP-13 and FKBP-12 which are capable of binding rapamycin and/or FK506 under conditions which allow binding of such drug(s) to FKBP-13. Such a chimera, defined as a polypeptide some portion or portions of which consist of FKBP-12-specific sequence and the remainder of which consists of FKBP-13-specific sequence, and generally referred to as a "chimera of FKBP-13" can be the same length as FKBP-13, or can be shorter (e.g., the same length as FKBP-12). It could even be as short as 77 amino acids, the minimal length of a fragment of FKBP-13 discussed above, so long as it includes the drug-binding region of FKBP-13 or -12 (or a chimera thereof) defined above. The chimera may be made by synthetic means, or by genetic engineering techniques as described above. FKBP-12-specific amino acid changes can be introduced into the cDNA encoding FKBP-13, or vice versa, using standard genetic engineering techniques. For example, a chimera identical to FKBP-12 except that amino acids 41, 42, 43, and 45 of FKBP-12 (corresponding to amino acids 48, 49, 50, and 52 of FKBP-13) were replaced with the corresponding FKBP-13 residues. This replacement was accomplished at the DNA level by PCR (polymerase chain reaction)-based site directed mutagenesis, using standard methodology. The DNA was then expressed by standard methods, and the chimeric protein was found in preliminary experiments to possess immunosuppressive drug-binding activity comparable to that of FKBP-12.

Other chimeras of FKBP-13 could contain some or all of the amino terminal seven residues and/or the carboxy terminal five residues of FKBP-13, for which there are no counterparts in FKBP-12, and/or could have any portion of the remainder of FKBP-13 replaced with FKBP-12 residues.

Screening for compounds capable of binding FKBP-13

FKBP-13 (or an FK506- or rapamycin-binding fragment or chimera thereof) purified as described above can be used to screen compounds for their ability to bind FKBP-13 as follows:

FKBP-13, or a fragment or chimera, can be attached to a matrix material suitable for an affinity column by standard methods (e.g., as described in Fretz et al., J. Am Chem. Soc. 113:1409–1411, 1991). Attachment via the amino terminus of the protein is preferred, as that would be less likely to interfere with the drug binding site near the carboxy terminus. Candidate compounds from any source are then contacted with the affinity matrix under conditions known to permit binding of rapamycin and/or FK506 to FKBP-13. After washing the matrix to remove all unbound material, binding of the compound can be detected and/or measured by standard means: e.g., by competition assays with detectably labelled rapamycin. Any compounds which appear by this assay to have FKBP-13-binding activity can then be tested in a cell-based assay such as one of those described on page 440 of Bierer et al., Eur. J. Immunol. 21:439–445, 1991 (hereby incorporated by reference), and the biological activity thereby compared to that of a known immunosuppressant drug such as rapamycin or FK506. If the candidate drug appears to have an effect on T-cells comparable to either known drug, it will be a promising candidate for more arduous in vivo trials.

The use of FKBP-13 (or a fragment thereof) complexed with FK506, rapamycin, or another FKBP-13-binding immunosuppressive drug, to screen for cellular constituents capable of binding to such complex It is believed that the immunosuppressive drugs rapamycin and FK506 act by complexing with an FKBP, and then binding to another cellular constituent to trigger immunosuppression in the subject animal. Identifying that cellular constituent is of considerable interest, both to aid in the understanding of the mechanism of immune suppression and to permit development of new drugs with improved properties. Liu et al. (Cell 66:807–815, 1991) have published a method of screening cellular lysates, using a recombinant fusion protein in which FKBP-12 is covalently attached via a peptide bond to the enzyme glutathione S-transferase, which binds to its ligand, glutathione, on a glutathione affinity column. The fusion protein, fixed on the column by means of its affinity for glutathione, is then contacted with FK506, which complexes with the FKBP-12 portion of the fusion protein. The column was then used to pull out of a cell lysate a cellular constituent, calcineurin, capable of binding to the FKBP-12/FK506 complex. This method can be directly adapted to employ FKBP-13 instead of FKBP-12, and rapamycin or other FKBP-13-binding drugs as well as FK506. To maximize the possibility that a cellular constituent of biological significance will bind to the complex, the assay could be further adapted to have the fusion protein expressed directly within the cells of interest (e.g., T-cells or renal cells). After treating the cells with the drug, the cells are lysed and the lysate containing the fusion protein/drug/cellular constituent complex is passed over the glutathione affinity column. These techniques are useful for studying the mechanism by which FK506 and rapamycin act both in T-cells, where they cause immunosuppression, and in kidney, brain and other tissues, where they exert a toxic effect. Thus, the invention includes such a screening method employing FKBP-13; a recombinant fusion protein in which FKBP-13, or a drug-binding fragment or chimera thereof, is linked to a second polypeptide such as glutathione S-transferase; a recombinant DNA molecule encoding such a fusion protein; and a matrix material onto which is bound (a) FKBP-13, (b) a drug-binding fragment or chimera thereof, or (c) a recombinant fusion protein including FKBP-13 or a drug-binding fragment or chimera thereof.

Antibodies to FKBP-13

Polyclonal or monoclonal antibodies specific for an epitope or epitopes within the amino-terminal portion of FKBP-13 can be prepared by standard immunological methods, by using a recombinant polypeptide consisting of all or a portion of the amino-terminal 35 amino acids of FKBP-13. Such antibodies are useful for immunoassays of FKBP-13 bound to rapamycin or FK506, for the amino terminal portion of FKBP-13 is not involved in binding the drugs. They are also useful for distinguishing between FKBP-13 and FKBP-12, which do not resemble each other in their amino terminal regions. Antibodies useful for the latter purpose can also be raised by using FKBP-13 as the antigen, and then selecting hybridomas producing antibodies which bind to FKBP-13 and not to FKBP-12.

Other embodiments are within the following claims.

---

We claim:

1. A substantially purified mammalian FKBP-13, which (1) has the sequence of an FK506-binding immunophilin naturally expressed in lymphocytes, (2) has an actual molecular weight between 10 and 15 kDa, and (3) has at least 80% sequence identity with residues 1 to 120 or residues −21 to 120 of human FKBP-13 (SEQ ID NO:6).

2. The mammalian FKBP-13 of claim 1, wherein said mammalian FKBP-13 has an amino acid sequence comprising that of precursor FKBP-13 (residues -21 to 120 of SEQ ID NO:6).

3. The mammalian FKBP-13 of claim 1, wherein said mammalian FKBP-13 has an amino acid sequence comprising that of the mature form of human FKBP-13 (residues 1 to 120 of SEQ ID NO:6).

4. The mammalian FKBP-13 of claim 1, wherein said mammalian FKBP-13 has an amino acid sequence identical to that of precursor FKBP-13 (residues -21 to 120 of SEQ ID NO:6).

5. The mammalian FKBP-13 of claim 1, wherein said mammalian FKBP-13 has an amino acid sequence identical to that of the mature form of human FKBP-13 (residues 1–120 of SEQ ID NO:6).

6. The mammalian FKBP-13 of claim 1, wherein said mammalian FKBP-13 comprises a sequence at least 90% identical to residues 33 to 115 of SEQ ID NO:6.

7. The mammalian FKBP-13 of claim 1, wherein said mammalian FKBP-13 is produced by recombinant means.

8. A composition comprising a mammalian FKBP-13 according to claim 1 in a pharmaceutically-acceptable carrier.

9. A rapamycin-binding fragment of a mammalian FKBP-13, which mammalian FKBP-13 has (1) the sequence of an FK506-binding immunophilin naturally expressed in lymphocytes, (2) an actual molecular weight between 10 and 15 kDa, and (3) at least 80% sequence identity with residues 1–120 of human FKBP-13 (SEQ ID NO:6);

said fragment comprising an amino acid sequence having at least sequence identity with residues 36–112 of SEQ ID NO:6.

10. The fragment of claim 9, wherein said mammalian FKBP-13 is human FKBP-13.

11. The fragment of claim 9, wherein said fragment is produced by recombinant means.

12. An FK506-binding fragment of a mammalian FKBP-13, which mammalian FKBP-13 has (1) the sequence of an FK506-binding immunophilin naturally expressed in lymphocytes, (2) an actual molecular weight between 10 and 15 kDa, and (3) at least 80% sequence identity with residues 1–120 of human FKBP-13 (SEQ ID NO:6);

said fragment comprising an amino acid sequence having at least 80% sequence identity with residues 36–112 of SEQ ID NO:6.

13. The fragment of claim 12, wherein said mammalian FKBP-13 is human FKBP-13.

14. The fragment of claim 12, wherein said fragment is produced by recombinant means.

15. A substantially purified polypeptide comprising an amino acid sequence corresponding to amino acids 36 through 112 of human FKBP-13 (SEQ ID NO: 6).

16. The substantially purified polypeptide of claim 15, wherein said polypeptide comprises an additional sequence of at least ten amino acids not corresponding to any portion of human FKBP-13 (SEQ ID NO:6).

17. A polypeptide comprising an amino acid sequence corresponding to amino acids 36 through 112 of mature human FKBP-13 (SEQ ID NO:6) and an additional sequence of at least ten amino acids not corresponding to any portion of said mature human FKBP-13.

* * * * *

UNITED STATES PATENT AND TRADEMARK OFFICE
CERTIFICATE OF CORRECTION

PATENT NO. : 5,498,597
DATED : March 12, 1996
INVENTOR(S) : Steven J. Burakoff et al.

It is certified that error appears in the above-identified patent and that said Letters Patent is hereby corrected as shown below:

On the title page,
Under References Cited [56] (OTHER PUBLICATIONS)

Siekierka reference (first occurrence), "Mature" should be --Nature--.

Maki et al. reference, insert --5440- -- after ":".

Kay et al. reference, delete "Medline Immunology Today 12:137-140" and insert --*Immunology* 72:544-549--.

Insert --Morris et al., Medline *Immunology Today* 12:137-140, 1991--

Col. 5, line 17, after "Drawings" start new paragraph.

Col. 7, line 41, "XAR-film" should be --XAR-5 film--.

UNITED STATES PATENT AND TRADEMARK OFFICE
CERTIFICATE OF CORRECTION

PATENT NO. : 5,498,597
DATED : March 12, 1996
INVENTOR(S) : Steven J. Burakoff et al.

It is certified that error appears in the above-identified patent and that said Letters Patent is hereby corrected as shown below:

Col. 9, line 7 insert --RNA-- before "preparations".

In the Claims

Claim 9, Col. 18, line 32, insert --80%-- after "least".

Signed and Sealed this

Third Day of March, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 570
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GGCCGGGGTT GACTCCGGGG GCGCGGCGAG GAGAGAC ATG AGG CTG AGC TGG TTC       55
                                            Met Arg Leu Ser Trp Phe
                                                -20

CGG GTC CTG ACA GTA CTG TCC ATC TGC CTG AGC GCC GTG GCC AGC ACG      103
Arg Val Leu Thr Val Leu Ser Ile Cys Leu Ser Ala Val Ala Ser Thr
-15                      -10                  -5                 -1   1

GGG GCC GAG GGC AAA AGG AAG CTG CAG ATC GGG GTC AAG AAG CGG GTG      151
Gly Ala Glu Gly Lys Arg Lys Leu Gln Ile Gly Val Lys Lys Arg Val
                 5                   10                  15

GAC CAC TGT CCC ATC AAA TCG CGC AAA GGG GAT GTC CTG CAC ATG CAC      199
Asp His Cys Pro Ile Lys Ser Arg Lys Gly Asp Val Leu His Met His
            20                  25                  30

TAC ACG GGG AAG CTG GAA GAT GGG ACA GAG TTT GAC AGC AGC CTG CCC      247
Tyr Thr Gly Lys Leu Glu Asp Gly Thr Glu Phe Asp Ser Ser Leu Pro
        35                  40                  45

CAG AAC CAG CCC TTT GTC TTC TCC CTT GGC ACA GGC CAG GTC ATC AAG      295
Gln Asn Gln Pro Phe Val Phe Ser Leu Gly Thr Gly Gln Val Ile Lys
50                   55                  60                  65

GGC TGG GAC CAG GGG CTG CTG GGG ATG TGT GAG GGG GAA AAG CGC AAG      343
Gly Trp Asp Gln Gly Leu Leu Gly Met Cys Glu Gly Glu Lys Arg Lys
                70                  75                  80

CTG GTG ATC CCA TCC GAG CTA GGG TAT GGA GAG CGG GGA GCT CCC CCA      391
Leu Val Ile Pro Ser Glu Leu Gly Tyr Gly Glu Arg Gly Ala Pro Pro
            85                  90                  95

AAG ATT CCA GGC GGT GCA ACC CTG GTG TTC GAG GTG GAG CTG CTC AAA      439
Lys Ile Pro Gly Gly Ala Thr Leu Val Phe Glu Val Glu Leu Leu Lys
        100                 105                 110

ATA GAG CGA CGA ACT GAG CTG TAACCAGACT GGGAGGGGCA GGGGAGAGGC         490
Ile Glu Arg Arg Thr Glu Leu
    115                 120

CCCCATCAGG ACCAGACTGT TCCAAAAAAA AAAAACAAA AAACAAACAA AAAAACACTT     550

AAAAAAAAAA AAAAAAAAA                                                 570
```

( 2 ) INFORMATION FOR SEQ ID NO: 2:

( i ) SEQUENCE CHARACTERISTICS:
        ( A ) LENGTH: 17
        ( B ) TYPE: nucleic acid
        ( C ) STRANDEDNESS: single (D) TOPOLOGY: linear (xi) SEQUENCE DESCRIPTION: SEQ ID NO: 2:

GARGGKAARM GNAARCY                                                                17

(2) INFORMATION FOR SEQ ID NO: 3:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 3:

CCNGTRTART GCATRTG                                                                17

(2) INFORMATION FOR SEQ ID NO: 4:

(i) SEQUENCE CHARACTERISTICS:
        (A) LENGTH: 40
        (B) TYPE: amino acid
        (C) STRANDEDNESS:
        (D) TOPOLOGY: linear (xi) SEQUENCE DESCRIPTION: SEQ ID NO: 4:

```
Thr Gly Thr Glu Gly Lys Arg Lys Leu Gln Ile Gly Val Lys Lys Arg
 1               5                  10                 15

Val Asp His Cys Pro Ile Lys Ser Arg Lys Gly Asp Val Leu His Met
            20                  25                  30

His Tyr Thr Gly Lys Leu Glu Asp
            35              40
```

(2) INFORMATION FOR SEQ ID NO: 5:

(i) SEQUENCE CHARACTERISTICS:
        (A) LENGTH: 108
        (B) TYPE: amino acid
        (C) STRANDEDNESS:
        (D) TOPOLOGY: linear (xi) SEQUENCE DESCRIPTION: SEQ ID NO: 5:

```
Met Gly Val Gln Val Glu Thr Ile Ser Pro Gly Asp Gly Arg Thr Phe
                 5                  10                 15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                      70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
                100                 105
```

(2) INFORMATION FOR SEQ ID NO:6:

(i) SEQUENCE CHARACTERISTICS:
        (A) LENGTH: 141 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

```
Met Arg Leu Ser Trp Phe Arg Val Leu Thr Val Leu Ser Ile Cys Leu
 1               5                  10                  15
Ser Ala Val Ala Ser Thr Gly Ala Glu Gly Lys Arg Lys Leu Gln Ile
            20                  25                  30
Gly Val Lys Lys Arg Val Asp His Cys Pro Ile Lys Ser Arg Lys Gly
        35                  40              45
Asp Val Leu His Met His Tyr Thr Gly Lys Leu Glu Asp Gly Thr Glu
    50                  55                  60
Phe Asp Ser Ser Leu Pro Gln Asn Gln Pro Phe Val Phe Ser Leu Gly
65                  70                  75                  80
Thr Gly Gln Val Ile Lys Gly Trp Asp Gln Gly Leu Leu Gly Met Cys
                85                  90                  95
Glu Gly Glu Lys Arg Lys Leu Val Ile Pro Ser Glu Leu Gly Tyr Gly
            100                 105                 110
Glu Arg Gly Ala Pro Pro Lys Ile Pro Gly Gly Ala Thr Leu Val Phe
        115                 120                 125
Glu Val Glu Leu Leu Lys Ile Glu Arg Arg Thr Glu Leu
    130                 135                 140
```